(12) United States Patent
Mirkin et al.

(10) Patent No.: US 7,829,735 B2
(45) Date of Patent: Nov. 9, 2010

(54) UNIVERSAL PHOSPHORAMIDITE FOR PREPARATION OF MODIFIED BIOMOLECULES AND SURFACES

(75) Inventors: Chad A. Mirkin, Wilmette, IL (US); Robert Elghanian, Wilmette, IL (US)

(73) Assignee: Northwestern University, Evansion, IL (US)

( * ) Notice: Subject to any disclaimer, the term of this patent is extended or adjusted under 35 U.S.C. 154(b) by 136 days.

(21) Appl. No.: 12/258,640

(22) Filed: Oct. 27, 2008

(65) Prior Publication Data

US 2009/0130455 A1    May 21, 2009

Related U.S. Application Data

(60) Provisional application No. 60/982,794, filed on Oct. 26, 2007.

(51) Int. Cl.
*C07F 9/02* (2006.01)
(52) U.S. Cl. .................. 558/45; 428/426; 536/124
(58) Field of Classification Search .................. 558/45; 428/426; 536/124
See application file for complete search history.

(56) References Cited

U.S. PATENT DOCUMENTS

| | | | |
|---|---|---|---|
| 4,415,732 A | 11/1983 | Caruthers et al. | |
| 5,324,831 A | 6/1994 | Marquez et al. | |
| 6,053,171 A | 4/2000 | Stewart et al. | |
| 6,136,568 A | 10/2000 | Hiatt et al. | |
| 6,140,127 A | 10/2000 | Sprague | |
| 6,355,270 B1 | 3/2002 | Ferrari et al. | |
| 6,361,944 B1 | 3/2002 | Mirkin et al. | |
| 6,417,340 B1 | 7/2002 | Mirkin et al. | |
| 6,495,324 B1 | 12/2002 | Mirkin et al. | |
| 6,506,564 B1 | 1/2003 | Mirkin et al. | |
| 6,582,921 B2 | 6/2003 | Mirkin et al. | |
| 6,610,491 B2 | 8/2003 | Mirkin et al. | |
| 6,635,311 B1 | 10/2003 | Mirkin et al. | |
| 6,645,721 B2 | 11/2003 | Mirkin et al. | |
| 6,673,548 B2 | 1/2004 | Mirkin et al. | |
| 6,677,122 B2 | 1/2004 | Mirkin et al. | |
| 6,682,895 B2 | 1/2004 | Mirkin et al. | |
| 6,709,825 B2 | 3/2004 | Mirkin et al. | |
| 6,720,147 B2 | 4/2004 | Mirkin et al. | |
| 6,720,411 B2 | 4/2004 | Mirkin et al. | |
| 6,726,847 B2 | 4/2004 | Mirkin et al. | |
| 6,730,269 B2 | 5/2004 | Mirkin et al. | |
| 6,740,491 B2 | 5/2004 | Mirkin et al. | |
| 6,750,016 B2 | 6/2004 | Mirkin et al. | |
| 6,759,199 B2 | 7/2004 | Mirkin et al. | |
| 6,767,702 B2 | 7/2004 | Mirkin et al. | |
| 6,773,884 B2 | 8/2004 | Mirkin et al. | |
| 6,777,186 B2 | 8/2004 | Mirkin et al. | |
| 6,812,334 B1 | 11/2004 | Mirkin et al. | |
| 6,818,753 B2 | 11/2004 | Mirkin et al. | |
| 6,827,979 B2 | 12/2004 | Mirkin et al. | |
| 6,828,432 B2 | 12/2004 | Mirkin et al. | |
| 6,858,387 B1 | 2/2005 | Smith et al. | |
| 6,861,221 B2 | 3/2005 | Mirkin et al. | |
| 6,878,814 B2 | 4/2005 | Mirkin et al. | |
| 6,902,895 B2 | 6/2005 | Mirkin et al. | |
| 6,903,207 B2 | 6/2005 | Mirkin et al. | |
| 6,962,786 B2 | 11/2005 | Mirkin et al. | |
| 6,969,761 B2 | 11/2005 | Mirkin et al. | |
| 6,974,669 B2 | 12/2005 | Mirkin et al. | |
| 6,984,491 B2 | 1/2006 | Mirkin et al. | |
| 6,986,989 B2 | 1/2006 | Mirkin et al. | |
| 7,063,946 B2 | 6/2006 | Kenten et al. | |
| 7,098,320 B1 | 8/2006 | Mirkin et al. | |
| 7,223,833 B1 | 5/2007 | Nielsen et al. | |
| 2002/0127574 A1 | 9/2002 | Mirkin et al. | |
| 2002/0137058 A1 | 9/2002 | Mirkin et al. | |
| 2002/0137070 A1 | 9/2002 | Mirkin et al. | |
| 2002/0137071 A1 | 9/2002 | Mirkin et al. | |
| 2002/0137072 A1 | 9/2002 | Mirkin et al. | |
| 2002/0146720 A1 | 10/2002 | Mirkin et al. | |
| 2002/0155442 A1 | 10/2002 | Mirkin et al. | |
| 2002/0155458 A1 | 10/2002 | Mirkin et al. | |
| 2002/0155459 A1 | 10/2002 | Mirkin et al. | |
| 2002/0155461 A1 | 10/2002 | Mirkin et al. | |
| 2002/0155462 A1 | 10/2002 | Mirkin et al. | |
| 2002/0160381 A1 | 10/2002 | Mirkin et al. | |
| 2002/0164605 A1 | 11/2002 | Mirkin et al. | |
| 2002/0172953 A1 | 11/2002 | Mirkin et al. | |
| 2002/0177143 A1 | 11/2002 | Mirkin et al. | |
| 2002/0182611 A1 | 12/2002 | Mirkin et al. | |
| 2002/0182613 A1 | 12/2002 | Mirkin et al. | |
| 2002/0192687 A1 | 12/2002 | Mirkin et al. | |
| 2003/0022169 A1 | 1/2003 | Mirkin et al. | |
| 2003/0044805 A1 | 3/2003 | Mirkin et al. | |
| 2003/0049630 A1 | 3/2003 | Mirkin et al. | |
| 2003/0049631 A1 | 3/2003 | Mirkin et al. | |

(Continued)

FOREIGN PATENT DOCUMENTS

WO    WO-00/24782    5/2000

*Primary Examiner*—Kamal A Saeed
*Assistant Examiner*—Valerie Rodriguez-Garcia
(74) *Attorney, Agent, or Firm*—Marshall, Gerstein & Borun LLP

(57) ABSTRACT

Reagents useful for attaching biomolecules (e.g., proteins, oligonucleotides, and other biomolecules) to a surface, processes of attaching molecules to a surface to form modified surfaces using these reagents, and methods of detecting a target compound using these modified surfaces are disclosed.

15 Claims, No Drawings

U.S. PATENT DOCUMENTS

| | | |
|---|---|---|
| 2003/0054358 A1 | 3/2003 | Mirkin et al. |
| 2003/0059777 A1 | 3/2003 | Mirkin et al. |
| 2003/0068622 A1 | 4/2003 | Mirkin et al. |
| 2003/0087242 A1 | 5/2003 | Mirkin et al. |
| 2003/0113740 A1 | 6/2003 | Mirkin et al. |
| 2003/0124528 A1 | 7/2003 | Mirkin et al. |
| 2003/0129608 A1 | 7/2003 | Mirkin et al. |
| 2003/0143538 A1 | 7/2003 | Mirkin et al. |
| 2003/0148282 A1 | 8/2003 | Mirkin et al. |
| 2003/0180783 A1 | 9/2003 | Mirkin et al. |
| 2003/0207296 A1 | 11/2003 | Park et al. |
| 2004/0038255 A1 | 2/2004 | Mirkin et al. |
| 2004/0072231 A1 | 4/2004 | Mirkin et al. |
| 2004/0086897 A1 | 5/2004 | Mirkin et al. |
| 2004/0110220 A1 | 6/2004 | Mirkin et al. |
| 2004/0131843 A1 | 7/2004 | Mirkin et al. |
| 2005/0037397 A1 | 2/2005 | Mirkin et al. |
| 2005/0153357 A1 | 7/2005 | Eichler et al. |
| 2006/0040286 A1 | 2/2006 | Mirkin et al. |
| 2006/0051798 A1 | 3/2006 | Mirkin et al. |

UNIVERSAL PHOSPHORAMIDITE FOR PREPARATION OF MODIFIED BIOMOLECULES AND SURFACES

CROSS REFERENCE TO RELATED APPLICATIONS

This application claims the benefit of U.S. Provisional Application No. 60/982,794, filed Oct. 26, 2007, the disclosure of which is incorporated by reference in its entirety.

STATEMENT OF GOVERNMENT INTEREST

This invention was made with U.S. government support under Air Force Research Laboratory (AFRL) contract no. FA8650-06-C-7617. The government has certain rights in this invention.

FIELD OF THE INVENTION

The present invention provides reagents useful for attaching biomolecules to a surface and methods of attaching biomolecules to a surface using the disclosed reagents.

BACKGROUND

Attachment of polypeptides, proteins, antibodies, oligonucleotides, lipids, carbohydrates, and other biomolecules to surfaces has been achieved via a variety of means. Biomolecules attached to surfaces are useful in a variety of applications, e.g., purification, interaction studies, diagnosis, and development of therapeutics. See, e.g., U.S. Patent Publication Nos. 2005/0153357 and 2005/0037397, each of which is incorporated by reference in its entirety.

For oligonucleotides, processes and reagents have been developed which allow for attachment of the oligonucleotide only at the 5' position. However, new reagents and methods are needed which allow for more versatility in attaching a biomolecule to a surface, for example, attaching an oligonucleotide to a surface via its 3' end.

SUMMARY

Disclosed herein are reagents suitable for attaching a biomolecule to a surface and methods of attaching a biomolecule to a surface using a disclosed reagent. More specifically, a reagent of formula (I) is disclosed:

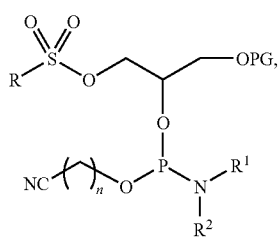

(I)

wherein R is hydrogen, alkyl, aryl, or haloalkyl; $R^1$ and $R^2$ can be the same or different and are independently selected from the group consisting of hydrogen and alkyl; PG is a hydroxyl protecting group; and n is an integer from 1 to 10. In specific embodiments, R is methyl, ethyl, isopropyl, phenyl, 4-methylphenyl, 4-trifluorophenyl, trifluoromethyl, or pentafluoroethyl. In specific embodiments, $R^1$ and $R^2$ independently are selected from the group consisting of methyl, ethyl, isopropyl, and propyl. In various embodiments, $R^1$ and $R^2$ are identical, and in more specific embodiments, both are isopropyl. In some embodiments, n is 1, 2, 3, or 4. In various embodiments, PG is a dimethoxytrityl or a silyl ether.

Another aspect of the invention provides a method of modifying a biomolecule comprising admixing the biomolecule and a compound of formula (I) as disclosed herein to form a modified biomolecule having a formula (IIA) or formula (IIB):

(IIA)

(IIB)

wherein R is hydrogen, alkyl, aryl, or haloalkyl; PG is a hydroxyl protecting group; and the biomolecule is selected from the group consisting of a polynucleotide, a polypeptide, a lipid, and a carbohydrate. In some embodiments, the biomolecule is an oligonucleotide and the oligonucleotide is modified at its 3' end. In certain embodiments, the oligonucleotide is modified at its 5' end.

Yet another aspect provides a method of preparing a modified surface comprising contacting a surface with a modified biomolecule as disclosed herein under conditions that permit modification of the surface to form a modified surface, wherein the modified surface has a formula (IIIA) or formula (IIIB),

(IIIA)

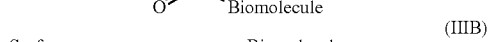

(IIIB)

wherein the biomolecule is selected from the group consisting of a polynucleotide, a polypeptide, a lipid, and a carbohydrate; and X is O, NH, or S.

In some embodiments, the surface comprises gold or glass having a moiety compatible with attaching the compound of formula (I) to its surface (e.g., a nucleophile or an azide). In some embodiments, the method further comprises contacting the modified surface with a target compound under conditions that permit interaction between the biomolecule on the modified surface and the target compound, wherein the interaction is detectable using an analytical technique selected from the group consisting of fluorescence, radioisotope detection, UV-Vis spectroscopy, and mass spectrometry. In some embodiments, the target compound comprises an antibody or an oligonucleotide.

Still another aspect provides a method of preparing a compound of formula (I) as disclosed herein comprising a) admixing a compound of formula (IV) and a protecting group reagent to form a compound of formula (V)

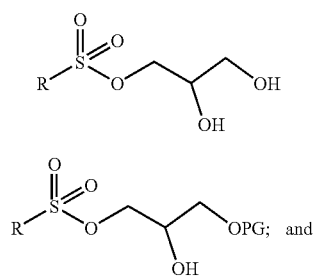

b) admixing the compound of formula (V) and $NC(CH_2)_n P(NR^1R^2)_2$ to form the compound of formula (I).

In some embodiments, the method further comprises admixing a compound of formula (VI) and an acid to form a compound of formula (IV):

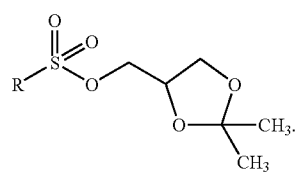

In certain embodiments, the method further comprises admixing 2,2-dimethyl-1,3-dioxolane-4-methanol and a $RSO_2Y$ reagent to form the compound of formula (VI), wherein Y is chloride, bromide, or iodide.

DETAILED DESCRIPTION

Disclosed herein are reagents useful for modifying biomolecules, methods of preparing these reagents, methods of modifying a biomolecule, and methods of modifying a surface using modified biomolecules. More particularly, disclosed herein are compounds of formula (I):

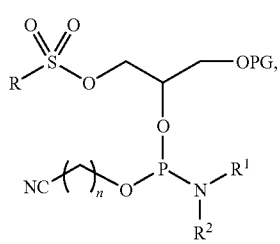

wherein R is hydrogen, alkyl, aryl, or haloalkyl; $R^1$ and $R^2$ can be the same or different and are independently selected from the group consisting of hydrogen and alkyl; PG is a hydroxyl protecting group; and n is an integer from 1 to 10. The compounds of formula (I) can be used as reagents to modify biomolecules, e.g., to form compounds of formula (IIA) or (IIB),

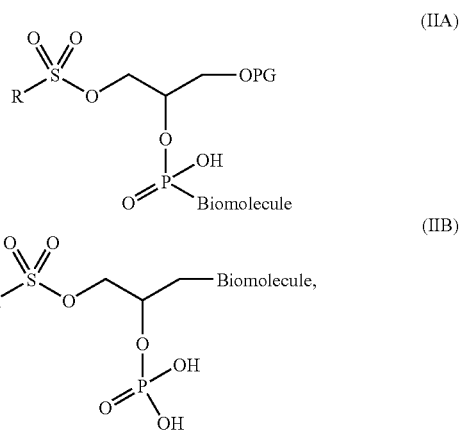

The compounds of formula (IIA) or (IIB) can be used to attach a biomolecule to a surface to provide a modified surface. Modified surfaces have many uses, for example, as diagnostic tools, in purification techniques, and modifications of surface properties to provide desired surface energies.

As used herein, the term "alkyl" refers to a linear or branched saturated hydrocarbon group containing 1 to 20 carbon atoms, preferably 1 to 10 carbon atoms, and more preferably 1 to 4 carbon atoms. Nonlimiting examples of alkyl moieties include methyl, ethyl, propyl, isopropyl, butyl, isobutyl, t-butyl, octyl, amyl, and the like.

As used herein, the term "aryl" refers to an aromatic moiety generally containing 6 to 30 carbon atoms and can include 1 to 4 heteroatoms (i.e., N, O, or S). An aryl group can contain a single aromatic ring or multiple aromatic rings either fused together, directly linked, or indirectly linked (such that the different aromatic rings are bound to a common group such as a methylene or ethylene moiety). Preferred aryl groups contain 6 to 20 carbon atoms, and particularly preferred aryl groups contain 6 to 12 carbon atoms. Nonlimiting examples of aryl groups containing one aromatic ring or two or more fused or linked aromatic rings include phenyl, naphthyl, biphenyl, diphenyl ether, diphenylamine, benzophenone, and the like. Aryl groups can optionally be substituted with one or more substituent groups. Nonlimiting examples of substituent groups include halo, nitro, cyano, linear or branched alkyl, linear or branched alkenyl, aryl, cycloalkyl, cycloalkenyl, amino, amido, carboxylate, and hydroxy.

The term "haloalkyl" refers to an alkyl group substituted with one or more halogen substitutents, such as fluoro, chloro, bromo, and/or iodo.

The term "hydroxyl protecting group" refers to a moiety that can be used to mask a hydroxyl group under certain reaction conditions in order to avoid modification or alteration of that hydroxyl protecting group, but can be removed to expose the hydroxyl group under other conditions. Generally, protecting groups are disclosed in Greene et al., *Protective Groups in Organic Synthesis*, 4th Ed. (John Wiley & Sons, Inc., New York, 2007. Nonlimiting examples of hydroxyl protecting groups include benzyl, paramethoxybenzyl, dimethoxytrityl, trityl, methoxymethyl, benzyloxymethyl, and silyl ethers, e.g., t-butyldimethylsilyl, trimethylsilyl, triethylsilyl, tri(isopropyl)silyl, and diphenylmethylsilyl.

The compounds of formula (I) can be synthesized according to reaction scheme of Scheme 1, below.

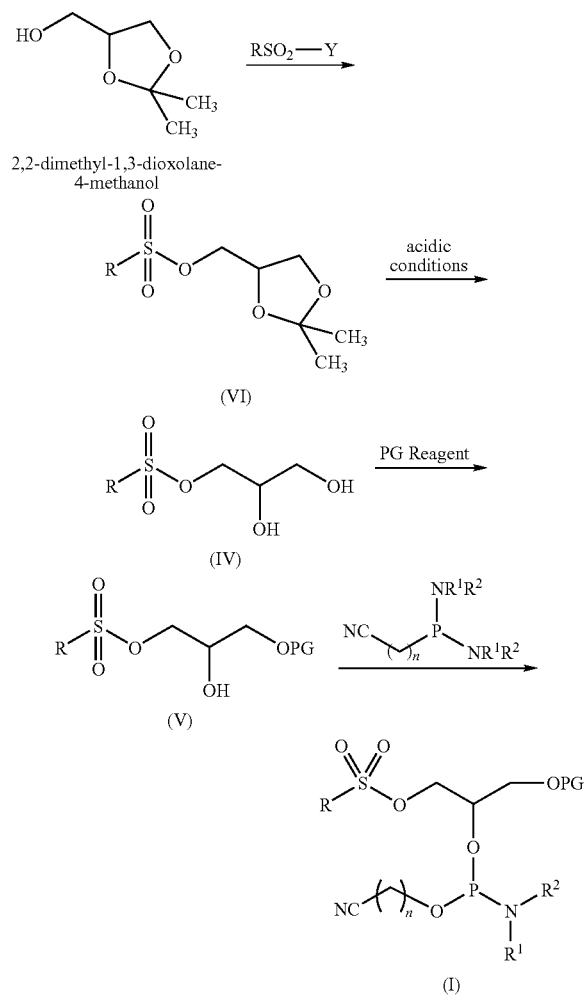

Sulfonyl reagents, $RSO_2Y$, are chosen to provide the desired R group in the compound of formula (I). Y is a leaving group, typically a halo, but can be any suitable leaving group known in the art which allows for formation of a compound of formula (VI).

Acidic conditions for formation of compounds of formula (IV) typically are mildly acidic (pH of about 4 to about 6.5), but can be more strongly acidic (pH of about 2 to about 4). Acidic conditions alternatively can be aprotic, such as an admixture of a compound of formula (VI) with a Lewis acid (e.g., metal chlorides, such as $AlCl_3$).

The protecting group reagent will depend upon the protecting group chosen. For example, when PG is a silyl ether, the corresponding silyl chloride can be admixed with the compound of formula (VI) to form a compound of formula (V). Alternatively, when PG is a dimethoxytrityl, dimethoxytrityl chloride is admixed with the compound of formula (VI) to form a compound of formula (V). Choice of appropriate protecting group reagents is based upon the desired protecting group of a compound of formula (V) or (I) and is within the knowledge of a person of skill in the art. Preferably, the protecting group reagent is admixed with the compound of formula (IV) under conditions which permit reaction of the protecting group reagent and the primary hydroxyl group rather than the secondary hydroxyl group, either selectively or predominantly. However, if the protected secondary hydroxyl group is formed, it can be separated from the compound of formula (V) by known techniques.

Conversion of a compound of formula (V) to a compound of formula (I) proceeds via formation of the phosphoramidite. A phosphoramidite reagent of formula $NC(CH_2)_nP(NR^1R^2)_2$ is admixed with a compound of formula (V) to form the compound of formula (I), where n is 1, 2, 3, 4, 5, 6, 7, 8, 9, or 10 and $R^1$ and $R^2$ are independently hydrogen or alkyl. The conditions for performing this reaction are disclosed in, e.g., U.S. Pat. Nos. 4,415,732; 5,324,831; and 6,136,568, each of which is incorporated by reference in its entirety.

The compounds of formula (I) can be used to modify a wider range of biomolecules than previously known methods. Because the compounds of formula (I) have two functional groups which can be used to modify a biomolecule of interest, a wider range of functionalities on biomolecules and surfaces can be modified. For example, the biomolecule can be modified using the hydroxyl group of the compound of formula (I) to form a compound of formula (IIB) or using the phosphoramidite functional group of the compound of formula (I) to form a compound of formula (IIA). Thus, biomolecules which can be functionalized via a hydroxyl group or a phosphoramidite can be modified using the disclosed compounds of formula (I).

Surfaces

The compounds of formula (I) can be used as a means to modify a surface with a biomolecule. Non-limiting examples of surfaces which can be modified using the disclosed compounds and useful in the disclosed methods include a thin film, a nanoparticle, and a nanoparticle on an otherwise inert surface.

Other nonlimiting examples of suitable surfaces include, but are not limited to, glass slides or other glass surfaces, polymer films, laminates, polymeric microparticles (including paramagnetic microparticles), metal and metal oxide surfaces, computer chips (such as silicon chips), natural and synthetic membranes, and other silica-based and plastic surfaces. In some cases, wherein the surface is glass, the glass may be treated with compound having a functional group such as an amine, carboxylate, thiol, hydroxyl, or anhydride, which provides a functional group capable of reaction with the compound of formula (IIA) or (IIB). Other surfaces can be similarly modified to provide a functional group to which the compound of formula (I), (IIA), or (IIB) can be attached. If the surface includes a gold micro- or nanoparticle surface, the surface may be modified with an functionalized alkylthiol to provide the appropriate functional group. Other functional groups may be introduced to the surface to provide, e.g., amines, alcohols, carboxylic acids, thiols, sulfonic acids, and the like, to the surface which allow for modification with the compound of formula (I), (IIA), and/or (IIB), to form, e.g., the compound of formula (IIIA) or (IIIB).

Amination, hydroxylation, carboxylation, and other modification of a surface (such as a polymeric surface) can be accomplished using corona discharge or a plasma glow discharge. Such methods are disclosed in, for example, U.S. Pat. Nos. 6,355,270; 6,140,127; and 6,053,171, each of which is incorporated in its entirety by reference herein.

Polymeric beads or surfaces can be, for example, polystyrene, polyethylene, polybutylene, polypropylene, polymerized mixed olefins, polyterpene, polyisoprene, polyvinyltoluene, poly($\alpha$-methylstyrene), poly(o-methylstyrene), poly(m-methylstyrene), poly(p-methylstyrene), poly (dimethylphenylene oxide), polyurethane, polyvinyl chloride, or mixtures thereof.

Methods for modifying a gold surface to attach functional groups such as those in compounds of formula (IIA) and/or (IIB) are known in the art, e.g., in U.S. Patent Publications 2006/0051798; 2006/0040286; 2005/0037397; 2004/0131843; 2004/0110220; 2004/0086897; 2004/0072231; 2004/0038255; 2003/0207296; 2003/0180783; 2003/0148282; 2003/0143538; 2003/0129608; 2003/0124528; 2003/0113740; 2003/0087242; 2003/0068622; 2003/0059777; 2003/0054358; 2003/0049631; 2003/0049630; 2003/0044805; 2003/0022169; 2002/0192687; 2002/0182613; 2002/0182611; 2002/0177143; 2002/0172953; 2002/0164605; 2002/0160381; 2002/0155462; 2002/0155461; 2002/0155459; 2002/0155458; 2002/0155442; 2002/0146720; 2002/0137072; 2002/0137071; 2002/0137070; 2002/0137058; 2002/0127574; each of which is incorporated herein in its entirety by reference.

Biomolecules

As used herein, the term "biomolecule" refers to a molecule having a functionality that can be modified using a reagent of formula (I). Typically, the biomolecule is isolated, but can be in a mixture containing other molecules which do not interfere with the modification of the biomolecule. Examples of functionality on a biomolecule include an alcohol moiety, thiol moiety, carboxylate, thiocarboxylate, and amine. Non-limiting examples of classes of biomolecules include polynucleotides, polypeptides, lipids, and carbohydrates.

As used herein, the term "polynucleotide" refers to a single-stranded polynucleotide of nucleobases. The term nucleobase, as used herein, is as defined in U.S. Pat. No. 7,223,833. Polynucleotides can be either natural or non-natural, or synthesized. Methods of making polynucleotides of a predetermined sequence are well-known. See, e.g., Sambrook et al., *Molecular Cloning: A Laboratory Manual* (2nd ed. 1989) and F. Eckstein (ed.) *Oligonucleotides and Analogues,* 1st Ed. (Oxford University Press, New York, 1991). Solid-phase synthesis methods are preferred for both polyribonucleotides and polydeoxyribonucleotides (the well-known methods of synthesizing DNA are also useful for synthesizing RNA). Polyribonucleotides and polydeoxyribonucleotides can also be prepared enzymatically.

In various aspects, the polynucleotide is an oligonucleotide. Oligonucleotides can have up to about 1000 nucleobases, up to about 700 nucleobases, up to about 500 nucleobases, or up to about 200 nucleobases. Other specific oligonucleotides include, but are not limited to, about 5 to about 100 nucleotides in length, about 5 to about 90 nucleotides in length. about 5 to about 80 nucleotides in length, about 5 to about 70 nucleotides in length, about 5 to about 60 nucleotides in length, about 5 to about 50 nucleotides in length, about 5 to about 45 nucleotides in length, about 5 to about 40 nucleotides in length, about 5 to about 35 nucleotides in length, about 5 to about 30 nucleotides in length, about 5 to about 25 nucleotides in length, about 5 to about 20 nucleotides in length, about 5 to about 15 nucleotides in length, or about 5 to about 10 nucleotides in length. Oligonucleotides include DNA oligonucleotides and RNA oligonucleotides.

Polypeptides include proteins and antibodies. Proteins include naturally-occurring proteins, i.e., proteins found in nature, synthetic proteins, i.e., proteins not found in nature, proteins that are partially naturally-occurring and partially synthetic, and fragments of each. Analogs of naturally occurring proteins are contemplated in the present invention, including polypeptides with modified glycosylation, polypeptides without glycosylation (unglycosylated). As used herein, "analogs" refers to an amino acid sequence that has insertions, deletions or substitutions relative to the parent sequence, while still substantially maintaining the biological activity of the parent sequence, as determined using biological assays known to one of skill in the art. The biomolecules and modified biomolecules as used herein may also include derivatives of naturally occurring or analog polypeptides which have been chemically modified, for example, to attach water soluble polymers (e.g., pegylated), radionuclides, or other diagnostic or targeting or therapeutic moieties.

Exemplary classes proteins include hormones, cytokines, hematopoietic factors, growth factors, antiobesity factors, trophic factors, anti-inflammatory factors, receptors or soluble receptors, and enzymes.

Herein, the term "antibody" is used in the broadest sense and includes fully assembled antibodies, monoclonal antibodies, polyclonal antibodies, multispecific antibodies (including bispecific antibodies), antibody fragments that can bind an antigen (including, Fab', F'(ab)$_2$, F$_v$, single chain antibodies, diabodies), and recombinant peptides comprising the foregoing as long as they exhibit the desired biological activity. Multimers or aggregates of intact molecules and/or fragments, including chemically derivatized antibodies, are contemplated. Antibodies of any isotype class or subclass, including IgG, IgM, IgD, IgA, and IgE, IgG1, IgG2, IgG3, IgG4, IgA1 and IgA2, or any allotype, are contemplated. Different isotypes have different effector functions; for example, IgG1 and IgG3 isotypes have antibody-dependent cellular cytotoxicity (ADCC) activity. Modification of synthetic antibodies is contemplated, including, for example and without limitation, substitution, addition, and deletion variants that maintain metal ion binding capacity through F$_c$ region interaction. The term "variant" when used in connection with antibodies refers to a polypeptide sequence of an antibody that contains at least one natural or non-natural amino acid substitution, deletion, addition or insertion in the variable region or the portion equivalent to the variable region, provided that the variant retains the desired binding affinity or biological activity. In addition, the antibodies of the invention may have amino acid modifications in the constant region to modify effector function of the antibody, including half-life or clearance, ADCC and/or CDC activity. Such modifications can enhance pharmacokinetics or enhance the effectiveness of the antibody in treating cancer, for example. See Shields et al., J. Biol. Chem., 276(9):6591-6604 (2001), incorporated by reference herein in its entirety. In the case of IgG1, modifications to the constant region, particularly the hinge or CH2 region, may increase or decrease effector function, including ADCC and/or CDC activity. In other embodiments, an IgG2 constant region is modified to decrease antibody-antigen aggregate formation. In the case of IgG4, modifications to the constant region, particularly the hinge region, may reduce the formation of half-antibodies. The term "derivative" refers to a molecule that is covalently modified by conjugation to therapeutic or diagnostic agents, labeling, and covalent polymer attachment. Derivatives of the invention will retain the binding properties of underivatized molecules of the invention. Still other antibody derivatives include antibody fusion proteins comprising an F$_c$ region and additional amino acid sequences, the additional amino acid sequence having a protein binding property. Such antibody fusion proteins are, in one aspect, produced by deletion of one or more antibody amino acid residues and addition of one or more other amino acid residues. For example and without limitation, a "chimeric" antibody includes all or part of an $F_c$ region from one antibody and all or part of an antigen binding $F_{ab}$ region from a second antibody. As another example, an antibody fusion protein includes all or part of an antibody $F_c$ region and amino acids from any source which binds a binding partner, possesses enzymatic activity or possesses any other biological property or activity. Accordingly, additional amino acids, and sequences comprising them, are naturally-occurring or synthetic, a full length protein, a protein fragment, a peptide and/or a derivative thereof as described above. Peptibodies are also contemplated. The term "peptibody" refers to a molecule comprising an antibody $F_c$ domain attached to at least one peptide. The production of peptibodies is generally described in PCT publication WO 00/24782, the disclosure of which is incorporated herein by reference.

The term "carbohydrate," as used herein, refers to a molecule having one or more sugar residues. Multiple sugar residues of a carbohydrate can be linked in either a straight chain or branched chain configuration. Carbohydrates composed of multiple sugar residues can vary in the type and location of the linkage between each residue. Sugar residues can include, but are not limited to, glucose, galactose, fucose, mannose, erythrose, threose, and sialic acid. Sugar residues also can be acetylated, phosphorylated or sulfated by chemically processes well known in the art. A carbohydrate also can be chemically bonded to other molecules such as a lipid, glycolipid, protein, glycoprotein, proteoglycan, glucosaminoglycan or an organic molecule. Carbohydrates can be naturally occurring or synthetically prepared.

The term "lipid," as used herein, refers to an organic molecule that includes fatty acids, glycerides (glycerol-derived lipids), non-glyceride lipids including steroids, phospholipids, prostaglandins, terpenes, waxes, which are generally solid at room temperature, and complex lipids such as lipoproteins and glycolipids. Lipids are generally liquid at room temperature and are more soluble in nonpolar solvents than in polar solvents. Fatty acids are long, unbranched monocarboxylic acids containing from about 10 to about 30 carbon atoms. Glycerides are lipid esters of the glycerol and possess a three carbon "backbone" of glycerol. Esterification may occur at one, two or all three OH locations, producing monoglycerides, diglycerides, and triglycerides, respectively. The fatty acid groups can be the same or different and may be saturated or unsaturated.

Detection of Target Compounds Using Modified Surfaces

The disclosed modified surfaces can be used in a variety of assays, including detection assays. Such detection assays are described in, e.g., U.S. Pat. Nos. 7,098,320; 7,063,946; 6,986,989; 6,974,669; 6,969,761; 6,962,786; 6,861,221; 6,858,387; 6,828,432; 6,827,979; 6,812,334; 6,777,186; 6,773,884; 6,767,702; 6,750,016; 6,730,269; 6,720,411; 6,720,147; 6,709,825; 6,682,895; 6,673,548; 6,645,721; 6,582,921; 6,506,564; 6,495,324; and 6,361,944, each of which is incorporated in its entirety by reference herein.

The choice of biomolecule to modify the surface will depend upon the target compound, and such choice is readily within the skill of one in the art. For example, for detection of an oligonucleotide target compound, the biomolecule on the modified surface can be a complementary oligonucleotide to the target compound, and for detection of an antigen, the surface of the composite particle can be modified with an appropriate antibodies. Conversely, for the detection of an antigen, the surface can be modified with an appropriate antibody.

As used herein, the term "target compound" refers to a compound of interest which is detectable using the modified surface disclosed herein. Typically, the target compound is an oligonucleotide, but can be any compound of interest which is detectable by the disclosed modified surface. Nonlimiting examples of target compounds include polynucleotides, antigens, antibodies, polypeptides, ionic compounds, metals, metal ions, and ligands.

In various aspects, the target compound is an oligonucleotide which is 100% complementary to an oligonucleotide of the modified surface, i.e., a perfect match, while in other aspects, the oligonucleotide is at least (meaning greater than or equal to) about 95% complementary to the target compound over the length of the oligonucleotide, at least about 90%, at least about 85%, at least about 80%, at least about 75%, at least about 70%, at least about 65%, at least about 60%, at least about 55%, at least about 50%, at least about 45%, at least about 40%, at least about 35%, at least about 30%, at least about 25%, at least about 20% complementary to the target compound over the length of the oligonucleotide to the extent that the oligonucleotide is able to achieve the desired degree of inhibition of a target gene product.

In various embodiments, the target compound comprises at least two portions. The lengths of these portions and the distance(s), if any, between them are chosen so that when the modified surface interacts with the target compound a detectable change occurs. These lengths and distances can be determined empirically and will depend on the type of surface used and its size and the type of electrolyte which will be present in solutions used in the assay. Also, when a target compound is to be detected in the presence of other oligonucleotides, the portions of the target to which the oligonucleotide(s) on oligonucleotide-modified surface is to bind must be chosen so that they contain a sufficiently unique sequence such that detection of the nucleic acid will be specific. These techniques are well known in the art and can be found, for example, in U.S. Pat. Nos. 6,986,989; 6,984,491; 6,974,669; 6,969,761; 6,962,786; 6,903,207; 6,902,895; 6,878,814; 6,861,221; 6,828,432; 6,827,979; 6,818,753; 6,812,334; 6,777,186; 6,773,884; 6,767,702; 6,759,199; 6,750,016; 6,740,491; 6,730,269; 6,726,847; 6,720,411; 6,720,147; 6,709,825; 6,682,895; 6,677,122; 6,673,548; 6,645,721; 6,635,311; 6,610,491; 6,582,921; 6,506,564; 6,495,324; 6,417,340; and 6,361,944, each of which is herein incorporated by reference in its entirety.

In embodiments where the target compound comprises an oligonucleotide, the detectable change that occurs upon hybridization of a target compound on an oligonucleotide-modified composite particle to the target can be a color change, formation of aggregates of the oligonucleotide-modified composite particles, and/or a precipitation of the aggregated oligonucleotide-modified surface. The color changes can be observed with the naked eye or spectroscopically. The formation of aggregates of the oligonucleotide-modified surface can be observed by electron microscopy, by nephelometry, or the eye. The precipitation of the aggregated oligonucleotide-modified surface can be observed with the naked eye or microscopically. Preferred are changes observable with the naked eye. Particularly preferred is a color change observable with the naked eye.

In certain embodiments, the target compound can be detected due to its association with the modified surface. In embodiments where the modified surface is magnetic, the complex of target compound and modified surface can be removed from a solution by application of a magnetic field. The target compound can be disassociated from the modified surface and detected using analytic techniques such as, for example, liquid chromatography, gas chromatography, mass spectrometry, gel electrophoresis, capillary electrophoresis, nuclear magnetic resonance, PCR, and the like.

Examples of the uses of the method for identifying a target compound include but are not limited to, the diagnosis and/or monitoring of viral diseases (e.g., human immunodeficiency virus, hepatitis viruses, herpes viruses, cytomegalovirus, and Epstein-Barr virus), bacterial diseases (e.g., tuberculosis, Lyme disease, *H. pylori, Escherichia coli* infections, *Legionella* infections, *Mycoplasma* infections, *Salmonella* infections), sexually transmitted diseases (e.g., gonorrhea), inherited disorders (e.g., cystic fibrosis, Duchene muscular dystrophy, phenylketonuria, sickle cell anemia), and cancers (e.g., genes associated with the development of cancer); in forensics; in DNA sequencing; for paternity testing; for cell line authentication; for monitoring gene therapy; and for many other purposes.

In various embodiments, the detection of a target compound is used in conjunction with drug discovery or DNA or oligonucleotide interacting compounds (e.g., intercalators and binders). A target compound can be assessed for its ability to specifically bind to a known biomolecule (e.g., polynucleotide, polypeptide, carbohydrate, or lipid) which is bound to the surface disclosed herein. The target compounds that bind or interact can be identified and isolated by applying a magnetic field, when the surface is magnetic. Upon disassociation from the surface, the target compound can be analyzed using common analytic techniques.

Examples of one class of target compounds that can be detected by the method of the present invention includes but is not limited to genes (e.g., a gene associated with a particular disease), viral RNA and DNA, bacterial DNA, fungal DNA, cDNA, mRNA, RNA and DNA fragments, oligonucleotides, synthetic oligonucleotides, modified oligonucleotides, single-stranded and double-stranded nucleic acids, natural and synthetic nucleic acids, and the like. The target compound may be isolated by known methods, or may be detected directly in cells, tissue samples, biological fluids (e.g., saliva, urine, blood, serum), solutions containing PCR components, solutions containing large excesses of oligonucleotides or high molecular weight DNA, and other samples, as also known in the art. See, e.g., Sambrook et al., *Molecular Cloning: A Laboratory Manual* (2nd ed. 1989) and B. D. Hames and S. J. Higgins, Eds., *Gene Probes* 1 (IRL Press, New York, 1995).

In other aspects, the target compound is a member of a specific binding pair which comprise nucleic acid, oligonucleotide, peptide nucleic acid, polypeptide, antibody, antigen, carbohydrate, protein, peptide, amino acid, hormone, steroid, vitamin, drug, virus, polysaccharides, lipids, lipopolysaccharides, glycoproteins, lipoproteins, nucleoproteins, oligonucleotides, antibodies, immunoglobulins, albumin, hemoglobin, coagulation factors, peptide and protein hormones, non-peptide hormones, interleukins, interferon, cytokines, peptides comprising a tumor-specific epitope, cells, cell-surface molecules, microorganisms, fragments, portions, components or products of microorganisms, small organic molecules, nucleic acids and oligonucleotides, metabolites of or antibodies to any of the above substances.

EXAMPLES

All reactions were carried out under an inert atmosphere of nitrogen. Anhydrous pyridine was purchased from Fluka and used as received. Deuterated solvents were purchased from Cambridge Isotope Laboratories Inc. and Aldrich and used as received. All other chemicals were used as received from Aldrich (compound VI) or prepared according to literature procedures (compounds VI, IV have appeared in the cited Japanese patent in the original disclosure). $^1$H, $^{31}$P NMR and $^{13}$C{$^1$H} NMR spectra were recorded on a Varian Mercury 300 MHz FT-NMR spectrometer at 300 MHz and 75.5 MHz, respectively and referenced to residual proton resonances in deuterated solvents. All chemical shifts are reported in ppm. Electron ionization mass spectra (EIMS) were recorded on a Fisions VG 70-250 SE mass spectrometer. Elemental analyses were performed by Quantitative Technologies Inc., Whitehouse, N.J. (USA).

Synthesis of (±)-2,3-Dihydroxypropyl tosylate (IV): 2,2-dimethyl-1,3-dioxolan-4-ylmethyl-p-toluenesulfonate (VI) (3.3 g) was dissolved in 80% acetic acid (5 mL) and allowed to react at 55° C. for 5 hours. The mixture was lyophilized to obtain a clear oil that slowly crystallized. The quantitative removal of the isopropylidine protecting group was verified by $^1$H NMR. (300 MHz, CDCl$_3$/D$_2$O). The proton NMR agreed well with previously published results.

Synthesis of (±)-1-O-Tosyl-3-O-(4,4'-dimethoxytrityl) glycerol (V): (±)-2,3-Dihydroxypropyl tosylate (IV) (525 mg, 2.13 mmol, 1 eq.) was dissolved in pyridine (20 mL, anhydrous) and cooled to 0° C. 4,4'-Dimethoxytrityl chloride (758 mg, 2.24 mmol, 1.05 eq.) was added in 3 portions over 2 h and the reaction solution was allowed to warm up to rt. After 2 h, sat. aq. NaHCO$_3$ (75 mL) was added to the reaction mixture, followed by extraction with CH$_2$Cl$_2$ (3×75 mL). The extract was dried with Na$_2$SO$_4$, filtered, concentrated in vacuo and dried by coevaporation with toluene (3×). Purification by flash column chromatography (SiO$_2$, 1:2:97 NEt$_3$/Et$_2$O/CH$_2$Cl$_2$) gave V as a white powder (770.6 mg, 66%). $^1$H NMR (300 MHz, CD$_2$Cl$_2$/D$_2$O): δ=7.74 (d, J=8.4 Hz, 2H, arom.), 7.36-7.21 (m, 11H, arom.), 6.82 (d, J=5.1 Hz, 4H, arom.), 4.10-3.98 (m, 2H, CH$_2$OTs), 3.92-3.89 (m, 1H, CHOH), 3.78 (s, 6H, OCH$_3$), 3.13-3.11 (m, 2H, CH$_2$ODMT), 2.44 (s, 3H, C$_6$H$_4$CH$_3$); $^{13}$C{$^1$H} NMR (75.5 MHz, CD$_2$Cl$_2$/D$_2$O): δ=159.3, 145.8, 145.3, 136.1, 133.1, 130.6, 129.6, 128.44, 128.41, 127.5, 127.4, 113.7, 86.9, 71.8, 69.3, 64.1, 55.8, 22.0; MS (EI): m/z. calcd for [C$_{31}$H$_{32}$O$_7$S]$^+$: 548.1869. found: 548.1867 [M]$^+$. elemental analysis calcd (%) for C$_{31}$H$_{32}$O$_7$S: C, 67.86; H, 5.88; found: C, 67.84; H, 5.93.

Synthesis of (±)-1-O-Tosyl-3-O-(4,4'-dimethoxytrityl) glycerol phosphoramidite (I): (±)-1-O-Tosyl-3-O-(4,4'-dimethoxytrityl)glycerol X (526 mg, 0.960 mmol) was dissolved in 15 mL of anhydrous dichloromethane. 2-cyanoethyl N,N,N',N',-tetraisopropylphosphoramidite (320 μL, 1 mmol) was added followed by addition of 1 mL of a saturated 4,5-dicyanoimidazole solution (1.3 g/10 mL) in acetonitrile. The mixture was allowed to react for three hours at room temperature after which it was extracted with 3×5 mL portions of 5% sodium bicarbonate solution. The organic layer was dried with anhydrous sodium sulfate, filtered and concentrated. Purification by flash chromatography (SiO$_2$, 1:99 NEt$_3$/Et$_2$OAc) gave I as a clear foam (700 mg, 96%). $^{31}$P NMR (300 MHz, CH$_3$XN) δ=150-151 as a mixture of diasteriomers.

Synthesis of tosylated oligonucleotides: Oligonucleotides were prepared via standard phosphoramidite synthesis using Ultramild reagents from Glen Research on 1 μmole scale. For 3' tosyl functionalization, the synthesis was started with a T support. 5' tosyl modification was introduced using a Universal Tosyl-phosphoramidite (I) at 1 mM concentration in dry acetonitrile manually with 10 min. coupling time. The oligonucleotide was the cleaved from the support in concentrated ammonium hydroxide at 55° C. for 15 min. followed by 1.5 hours of standing at room temperature. Ammonium hydroxide was removed under a stream of nitrogen. The crude product was then purified by HPLC (0.03M triethylammonium acetate, 95% $CH_3CN$/5% 0.03M triethylammonium acetate) using a 1%/minute gradient at a flow rate of 3 mL/min. on a reverse phase column. The oligonucleotide sequences modified were 3'-T-tosyl modifier-TTT-TTT-TTT-TTT-TTT-TTT-TT (MALDI, 6668) (SEQ ID NO: 1)

TTT-TTT-TTT-TTT-TTT-TTT-TT (MALDI, 6323) (SEQ ID NO: 2)

TTT-TTT-TTT-TTT-TTT-TTT-TT-tosyl modifier-DMT (MALDI, 6677) (SEQ ID NO: 3)

MALDI was performed using dihydroxyacetophenone as matrix. Since the matrix is acidic, the DMT group falls off during MALDI analysis. The presence of DMT was confirmed via HPLC as isolated.

The foregoing describes and exemplifies the invention but is not intended to limit the invention defined by the claims which follow. All of the methods disclosed and claimed herein can be made and executed without undue experimentation in light of the present disclosure. While the materials and methods of this invention have been described in terms of specific embodiments, it will be apparent to those of skill in the art that variations may be applied to the materials and/or methods and in the steps or in the sequence of steps of the methods described herein without departing from the concept, spirit and scope of the invention. More specifically, it will be apparent that certain agents which are both chemically and physiologically related may be substituted for the agents described herein while the same or similar results would be achieved.

What is claimed is:

1. A compound of formula (I):

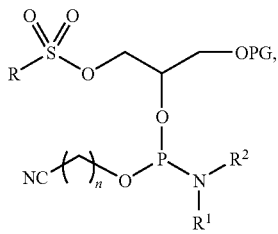

(I)

wherein R is hydrogen, alkyl, aryl, or haloalkyl; $R^1$ and $R^2$ can be the same or different and are independently selected from the group consisting of hydrogen and alkyl; PG is a hydroxyl protecting group; and n is an integer from 1 to 10.

2. The compound of claim 1, wherein PG is dimethyoxytrityl or silyl ether.

3. The compound of claim 1, wherein R is selected from the group consisting of methyl, ethyl, isopropyl, phenyl, 4-methylphenyl, 4-trifluorophenyl, trifluoromethyl, and pentafluoroethyl.

4. The compound of claim 1, wherein $R^1$ and $R^2$ each are independently selected from the group consisting of methyl, ethyl, isopropyl, and n-propyl.

5. The compound of claim 1, wherein n is an integer of 1 to 4.

6. The compound of claim 1, wherein $R^1$ and $R^2$ each are isopropyl.

7. The compound of claim 1, wherein the compound of formula (I) is:

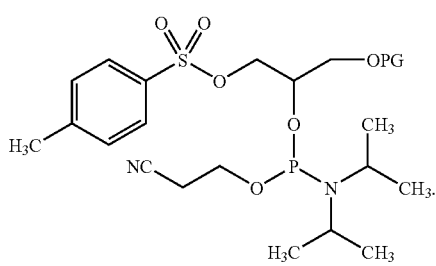

8. A method of preparing a compound of formula (I) comprising
   a) admixing a compound of formula (IV) and a protecting group reagent to form a compound of formula (V):

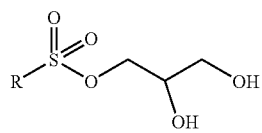

(IV)

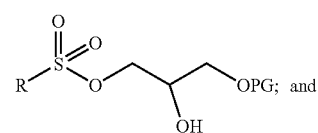

(V)

b) admixing the compound of formula (V) and a phosphoramidite of formula $NC(CH_2)_nP(NR^1R^2)_2$ to form the compound of formula (I):

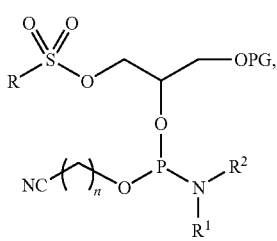

(I)

wherein R is hydrogen, alkyl, aryl, or haloalkyl; $R^1$ and $R^2$ can be the same or different and are independently selected from the group consisting of hydrogen and alkyl; PG is a hydroxyl protecting group; and n is an integer from 1 to 10.

9. The method of claim 8, wherein PG is dimethyoxytrityl or silyl ether.

10. The method of claim 8, wherein R is selected from the group consisting of methyl, ethyl, isopropyl, phenyl, 4-methylphenyl, 4-trifluorophenyl, trifluoromethyl, and pentafluoroethyl.

11. The method of claim 8, wherein $R^1$ and $R^2$ are each independently selected from the group consisting of methyl, ethyl, isopropyl, and n-propyl.

12. The method of claim 8, wherein n is an integer from 1 to 4.

13. The method of claim 8, wherein the compound of formula (I) is:

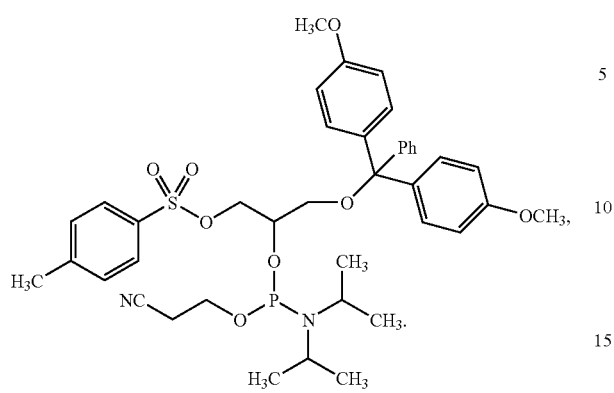
wherein Ph is phenyl.
14. The method of claim 8, further comprising admixing the compound of formula (VI) and an acid to form the compound of formula (IV)
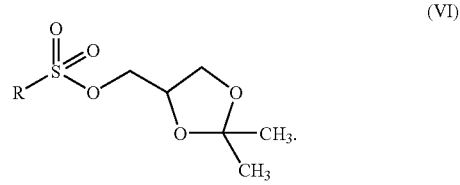
(VI)
15. The method of claim 14, further comprising admixing 2,2-dimethyl-1,3-dioxolane-4-methanol and a RSO$_2$Y reagent to form the compound of formula (VI), wherein Y is chloride, bromide, or iodide.
* * * * *

UNITED STATES PATENT AND TRADEMARK OFFICE
CERTIFICATE OF CORRECTION

PATENT NO. : 7,829,735 B2  Page 1 of 1
APPLICATION NO. : 12/258640
DATED : November 9, 2010
INVENTOR(S) : Chad A. Mirkin et al.

It is certified that error appears in the above-identified patent and that said Letters Patent is hereby corrected as shown below:

At column 1, line numbers 14-17, after "Statement of Government Interest" please replace the paragraph with the following:

This invention was made with government support under Grant No. FA8650-06-C-7617 awarded by the United States Air Force (AFMCLO/JAZI). The government has certain rights in the invention.

Signed and Sealed this
First Day of March, 2011

David J. Kappos
*Director of the United States Patent and Trademark Office*

```
                        SEQUENCE LISTING

<160> NUMBER OF SEQ ID NOS: 3

<210> SEQ ID NO 1
<211> LENGTH: 21
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (1)..(1)

<400> SEQUENCE: 1

Thr Thr Thr Thr Thr Thr Thr Thr Thr Thr Thr Thr Thr Thr Thr Thr
1               5                   10                  15

Thr Thr Thr Thr Thr
            20

<210> SEQ ID NO 2
<211> LENGTH: 20
<212> TYPE: PRT
<213> ORGANISM: Artificial Sequence
<220> FEATURE:
<223> OTHER INFORMATION: Synthetic Peptide

<400> SEQUENCE: 2

Thr Thr Thr Thr Thr Thr Thr Thr Thr Thr Thr Thr Thr Thr Thr Thr
1               5                   10                  15

Thr Thr Thr Thr
            20

<210> SEQ ID NO 3
<211> LENGTH: 20
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (20)..(20)

<400> SEQUENCE: 3
```

-continued

```
Thr Thr Thr Thr Thr Thr Thr Thr Thr Thr Thr Thr Thr Thr Thr
1               5                   10                  15

Thr Thr Thr Thr
            20
```